US011668692B2

(12) United States Patent
Loriau et al.

(10) Patent No.: US 11,668,692 B2
(45) Date of Patent: Jun. 6, 2023

(54) SCREENING METHOD FOR ASSESSING THE $H_2S$ RELEASE CAPACITY OF A SULFUR CONTAINING SAMPLE

(71) Applicant: TotalEnergies OneTech, Courbevoie (FR)

(72) Inventors: Matthieu Loriau, Lons (FR); David Mayou, Lescar (FR)

(73) Assignee: TotalEnergies OneTech, Courbevoie (FR)

( * ) Notice: Subject to any disclaimer, the term of this patent is extended or adjusted under 35 U.S.C. 154(b) by 758 days.

(21) Appl. No.: 16/500,838

(22) PCT Filed: Apr. 4, 2017

(86) PCT No.: PCT/IB2017/000497
§ 371 (c)(1),
(2) Date: Oct. 4, 2019

(87) PCT Pub. No.: WO2018/185510
PCT Pub. Date: Oct. 11, 2018

(65) Prior Publication Data
US 2020/0096492 A1    Mar. 26, 2020

(51) Int. Cl.
*G01N 33/28* (2006.01)
(52) U.S. Cl.
CPC ................ *G01N 33/287* (2013.01)
(58) Field of Classification Search
None
See application file for complete search history.

(56) References Cited

U.S. PATENT DOCUMENTS

| 5,922,087 A | 7/1999 | Nishioka et al. |
| 6,920,802 B2 * | 7/2005 | Newbound ............ G01N 7/10 73/863.25 |

(Continued)

FOREIGN PATENT DOCUMENTS

| DE | 197 41 809 A1 | 4/1999 |
| JP | 2011 169802 A | 9/2011 |

OTHER PUBLICATIONS

PCT International Search Report and Written Opinion of the ISA for PCT/IB2017/000497, dated Nov. 2, 2017, 13 pages.

(Continued)

*Primary Examiner* — Daniel S Larkin
(74) *Attorney, Agent, or Firm* — Patterson Thuente IP

(57) ABSTRACT

The present invention relates to method for assessing the $H_2S$ release capacity of a liquid sample containing one or more sulfur compounds which are able to be degraded into gaseous $H_2S$ with temperature. The method comprising: a) Placing a volume of the liquid sample in a purge vessel so as to obtain a liquid phase and a gaseous phase in a flask; b) Purging the gaseous phase with an inert gas stream for a determined period of time; e) Passing the purged gaseous phase through a $H_2S$ trap; d) Recovering $H_2S$ from the $H_2S$ trap; and e) Dosing the recovered $H_2S$. The invention is also used in a method for selecting a liquid sample, in particular among a group of different liquid samples.

10 Claims, 1 Drawing Sheet

(56) References Cited

U.S. PATENT DOCUMENTS

2014/0004611 A1* 1/2014 Feustel .............. G01N 33/287
436/60
2016/0090655 A1 3/2016 Pou et al.

OTHER PUBLICATIONS

Hwang Y et al: "Identification and quantification of sulfur and nitrogen containing odorous compounds in wastewater", Water Research, Elsevier, Amsterdam, NL, vol. 29, No. 2, Feb. 1995 (Feb. 1995), pp. 711-718, XP004035483, ISSN: 0043-1354, DOI: 10.1016/0043-1354(94)00145-W.

* cited by examiner

SCREENING METHOD FOR ASSESSING THE $H_2S$ RELEASE CAPACITY OF A SULFUR CONTAINING SAMPLE

RELATED APPLICATIONS

The present application is a National Phase entry of PCT Application No. PCT/IB2017/000497, filed Apr. 4, 2017, said application being hereby incorporated by reference herein in its entirety.

FIELD OF THE INVENTION

The invention relates to an analytical method and a screening method.

The invention relates in particular to a method for assessing the $H_2S$ release capacity of a liquid sample containing one or more sulfur compounds which are able to be degraded into gaseous $H_2S$ with temperature. Such method can be used in order to screen various liquid compositions, such as additives for the oil industry, and select the one which has the lowest $H_2S$ release capacity.

BACKGROUND OF THE INVENTION

The oil and gas industry employs corrosion inhibitor additives in order to protect oil and gas production installations against internal corrosion. These additives are commonly formulated as liquid blends of various chemical compounds, including sulfur compounds, such as thiols or thioethers. When stocked in a tank, the sulfur compounds contained in these additives can be thermally degraded, thereby leading to the production of $H_2S$. $H_2S$ is known to be harmful to humans and even deadly at concentrations as low as 500 ppm. Because it is heavier than air, the $H_2S$ released from the vent of an additive containing stock tank will accumulate on ground thereby creating a deadly atmosphere for people working in such an environment.

Portable $H_2S$ detectors are available that are able to detect the presence of $H_2S$ in the atmosphere. The detector can be a paper comprising lead acetate that becomes black in contact with $H_2S$ (formation of lead sulfur). The detector also can be an electrochemical detector able to detect a $H_2S$ level above a certain threshold value. However, these detectors are not able to measure the level of $H_2S$ in the atmosphere. Therefore, they cannot be used to determine which additives release the highest amounts of $H_2S$.

Experiments consisting of ageing an additive in a closed flask and analyzing the degradation product can be conducted in order to evaluate the quantity of $H_2S$ released from the additive over time (static headspace concentration). However, these experiments do not correctly simulate the real conditions of a stock tank having a vent. Indeed, in a closed flask, the degradation of the sulfur compounds occurs until equilibrium is reached. In a stock tank, the equilibrium can be never reached because $H_2S$ is evacuated through the vent. Therefore, the amount of $H_2S$ formed in a closed flask is lower than the one formed in a stock tank, and thus is not representative of real conditions. Moreover, such experiments are not easy to handle because they require different steps such as taking a sample of the degradation product and analyzing the sample into a gas chromatography. These steps must be performed by a well-trained operator under safety conditions in order to avoid the contamination of the degradation product or because the handled products are dangerous. Furthermore, these experiments are time consuming.

Consequently, there is a need for a method for assessing the amount of $H_2S$ released from a sample under conditions which can simulate the conditions in a stock tank and which does not require de-formulation of said sample (i.e. build up the formulation of the sample).

There is also a need for a method for screening various liquid samples and select the one which has the lowest $H_2S$ release capacity.

The invention meets this need by providing a method which is fast, easy to carry out and safe.

SUMMARY OF THE INVENTION

A first object of the present invention is a method for assessing the $H_2S$ release capacity of a liquid sample containing one or more sulfur compounds which are able to be degraded into gaseous $H_2S$ with temperature, said method comprising the following steps:
a) Placing a volume of the liquid sample in a purge vessel so as to obtain a liquid phase and a gaseous phase in a flask;
b) Purging the gaseous phase with an inert gas stream for a determined period of time;
c) Passing the purged gaseous phase through a $H_2S$ trap;
d) Recovering $H_2S$ from the $H_2S$ trap; and
e) Dosing the recovered $H_2S$.

In one embodiment, the liquid sample has a boiling temperature of at least 80° C.

In one embodiment, the purge vessel is kept at a temperature from 40° C. to 60° C., in particular from 45° C. to 55° C.

In one embodiment, the period of time of the purging step b) is from 2 min to 12 min, in particular from 3 min to 10 min, more particularly from 5 min to 8 min.

In one embodiment, the trapping step c) is performed by cryofocusing, adsorption, gas-solid reaction with a captation mass, in particular by cryofocusing on a polymeric non-polar adsorbent with liquid nitrogen.

In one embodiment, the dosing step d) is performed by gas chromatography possibly coupled with mass spectrometry, thermogravimetric analysis possibly coupled with mass spectrometry, elemental analysis for sulfur, in particular by gas chromatography coupled with mass spectrometry.

A second object of the invention is a method for selecting a liquid sample among a group of different liquid samples, said method comprising the following steps:
Assessing the $H_2S$ release capacity of each liquid sample according to the method previously described; and
Selecting the sample which has the lowest $H_2S$ release capacity.

A third object of the invention is a method for selecting a liquid sample, said method comprising the following steps:
Assessing the $H_2S$ release capacity of each liquid sample according to the method previously described; and
Comparing the $H_2S$ release capacity with a threshold value.

DETAILED DESCRIPTION OF THE INVENTION

A first aspect of the invention is a method for assessing the $H_2S$ release capacity of a liquid sample containing one or more sulfur compounds which are able to be degraded into gaseous $H_2S$ with temperature, said method comprising the following steps:

a) Placing a volume of the liquid sample in a purge vessel so as to obtain a liquid phase and a gaseous phase in a flask;

b) Purging the gaseous phase with an inert gas stream for a determined period of time;

c) Passing the purged gaseous phase through a $H_2S$ trap;

d) Recovering $H_2S$ from the $H_2S$ trap;

e) Dosing the recovered $H_2S$.

The method of the invention can be applied to any liquid composition comprising one or more sulfur compounds which are able to be degraded into gaseous $H_2S$ with temperature, i.e. by thermolysis.

By "sulfur compound", it is meant a compound containing one or more sulfur atoms. In one embodiment, the sulfur compound is a thiol, a thio-ether, or a thioacid.

The liquid sample may be an additive for the oil industry, such as a corrosion inhibitor, an oil wetting agent, a solid dispersing agent, a scale inhibitor, an anti-foulant, an oxygen scavenger, a foaming agent, or a mixture thereof. These additives are commonly formulated as liquid blends of various chemical compounds, including sulfur compounds, such as thiols or thioethers. But the method of the invention is not limited to these additives and can be applied to any liquid composition able to release gaseous $H_2S$ under storage conditions.

By "liquid sample" or "liquid composition", it is meant a sample or composition which is liquid under normal conditions of use and storage, i.e. under atmospheric pressure and at 25° C. By "$H_2S$ release capacity", it is meant the amount of $H_2S$ released by a given amount of sample during a given period of time for a given temperature, under atmospheric pressure. The method of the invention enables determining the amount of $H_2S$ which is released by a sample under conditions which simulate the real conditions under which the sample is stored.

Alternatively, the method of the invention can be used to screen and compare the $H_2S$ release capacity of various samples, and to select the one which has the lowest $H_2S$ release capacity. In that case, the quantitative analysis of the $H_2S$ release capacity is not necessary.

According to step (a), a volume of the liquid sample is placed in a purge vessel so as to obtain a liquid phase and a gaseous phase in the flask.

In order to implement the method of the invention, a dynamic headspace technique, such as a Purge and Trap device, can be utilized.

Purge and Trap devices are typically used for extracting volatile organic compounds (VOCs) from a solid or a liquid matrix. They are generally combined with an analysis system for analyzing the desorbed compounds, such as a Gas Chromatograph.

Figure 1:
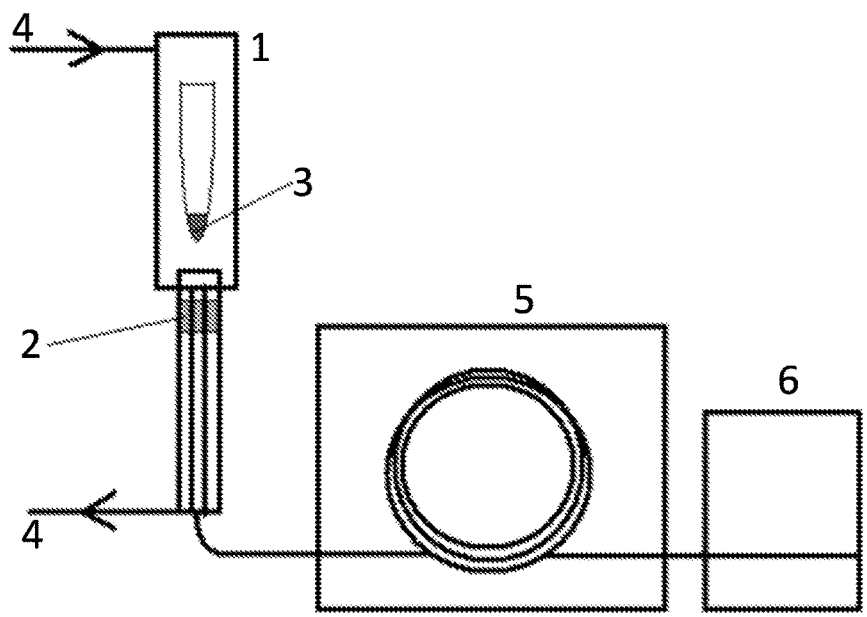
FIG. 1 is schematic representation of an apparatus for carrying out the method of the invention.

FIG. 1 represents a Purge and Trap device coupled to a Gas Chromatograph/Mass Spectrometer (GC/MS). The Purge and Trap device mainly consists of two pieces of equipment: an oven 1 having a gas inlet and a gas outlet and a trapping and desorbing unit 2 in fluid communication with the oven 1. The oven 1 is configured to receive the purge vessel 3 containing the liquid sample to be analyzed. A flow of inert gas 4 is then introduced in the oven 1 through the gas inlet to purge the oven atmosphere at a constant flow rate for a determined time (purging step). This way, the inert gas stream makes contact with the sample. This process allows the inert gas stream to strip the gaseous $H_2S$ released from the sample matrix through the gas outlet of the oven 1 and to concentrate it on a $H_2S$ trap of the trapping and desorbing unit 2. Once the purging step is over, all the trapped molecules are desorbed and sent to the GC/MS 5 and 6 for analysis, as described in more details below.

In one embodiment, the liquid phase and the gaseous phase are obtained by ageing the liquid sample in the purge vessel at a given temperature.

Additives for the oil industry are usually stored on the petroleum site and thus can be exposed to relatively high temperatures (from 40° C. to 50° C.), especially when the petroleum site in a hot country. Therefore, the purge vessel may be required to be heated in order to reproduce the storage conditions.

Typically, ageing of the liquid sample is performed by heating the purge vessel at a temperature from 40° C. to 60° C., more particularly from 45° C. to 55° C., during a period of time ranging from 1 min. to 30 min., in particular from 2 min. to 10 min., more particularly from 4 min. to 6 min.

If the purge vessel is not heated, the amount of $H_2S$ released from the liquid sample may be too low to be easily analyzed.

In one embodiment, the volume of liquid sample placed in the purge vessel is from 1 μL to 300 μL, in particular from 5 μL to 100 μL.

According to the invention, the gaseous phase is then purged with an inert gas stream for a determined period of time (step b) and the purged gaseous phase is passed through a $H_2S$ trap (step c).

The flow rate of the inert gas stream for the purge and trap of steps b) or c) can be from 20 mL/min. to 90 mL/min., in particular from 50 mL/min. to 70 mL/min.

The inert gas is preferably chosen from helium, nitrogen, or hydrogen. When the Purge and Trap device is coupled to a Gas Chromatograph, the inert gas is preferably the same as the one used in the Gas Chromatograph, typically helium.

According to the invention, during the purging step b), the purge vessel can be kept at a temperature from 40° C. to 60° C., more particularly from 45° C. to 55° C.

The duration of the purging step b) can be performed during a period of time ranging from 1 min to 30 min, in particular from 2 min to 10 min, more particularly from 4 min to 6 min.

In practice, the temperature of the purge vessel and the flow rate of the inert gas are adjusted so that the duration of the purging step b) is only a few minutes, thereby allowing a rapid screening of a large number of liquid samples.

In a preferred embodiment, the operating conditions are the following ones:
  volume of the liquid sample: from 5 μL to 100 μL,
  temperature of the purge vessel is from 45° C. to 55° C., preferably around 50° C.,
  duration of the purging step b): from 4 min to 6 min, around 5 minutes, and
  flow rate of the inert gas: from 50 mL/min. to 70 mL/min., preferably around 60 mL/min.

The purged gaseous phase that contains $H_2S$ released from the sample is passed through the $H_2S$ trap where it is concentrated (step c).

The $H_2S$ trap may be any device which is able to retain gaseous $H_2S$ during the entire purging step and then to rapidly release it during the recovery step d).

The concentration of $H_2S$ on the $H_2S$ trap may be performed by cryofocusing, adsorption, absorption, gas-solid reaction with a captation mass, in particular by cryofocusing on a polymeric non-polar adsorbent, such as Tenax® adsorbent.

Cryofocusing is a technique that can rapidly and specifically trap all the $H_2S$ contained in the gaseous phase. It can be performed with liquid nitrogen.

In one embodiment, cryofocusing is performed at a temperature below the $H_2S$ condensing temperature (−85.7° C.) but above the inert gas condensing temperature so that only $H_2S$ is trapped by cryofocusing. The cryofocusing can performed at a temperature from −150° C. to −50° C., more particularly from −125° C. to −60° C., even more particularly from −105° C. to −86° C. Alternatively, $H_2S$ can be trapped by a sorbent material. By "sorbent material", it is meant any solid which is able to selectively adsorb or absorb $H_2S$, such as $ZnO$, $CuO$, $Cu_2O$, $MoO_3$.

The trapped $H_2S$ is then recovered from the $H_2S$ trap (step d)). Any suitable method can be used. For instance, $H_2S$ can be recovered by thermo-desorption if cryofocalisation is used to trap $H_2S$.

Thermo-desorption is typically performed by passing an inert gas stream through the $H_2S$ trap while heating said $H_2S$ trap.

Typically, the flow rate of the inert gas stream during the thermo-desorption is below 5 mL/min, in particular from 0.1 mL/min to 3 mL/min, more particularly from 0.5 mL/min to 2 mL/min.

Typically, the $H_2S$ trap is heated from temperature T1 to temperature T2, wherein T2 is higher than T1, at a heating rate from 1° C./s to 50° C./s, in particular from 5° C./s to 20° C./s, more particularly from 10° C./s to 15° C./s.

Typically T1 is from 50° C. to 150° C., in particular from 75° C. to 125° C., more particularly from 90° C. to 110° C. Typically T2 is from 250° C. to 350° C., in particular from 275° C. to 325° C., more particularly from 290° C. to 310° C.

The recovered $H_2S$ is then dosed (step e)). Any suitable analytical method can be used.

The dosing step e) can be performed for instance by gas chromatography possibly coupled with mass spectrometry, thermogravimetric analysis possibly coupled with mass spectrometry, elemental analysis for sulfur.

Preferably, the dosing step e) is performed by gas chromatography coupled with mass spectrometry.

The dosage can be quantitative or semi-quantitative. A semi-quantitative dosage does not require the time consuming step of calibration.

When the dosage is quantitative, the amount of $H_2S$ released by a given amount of sample during a given period of time for a given temperature, under atmospheric pressure can be quantitatively determined.

When the dosage is semi-quantitative, the method of the invention can be used to compare the $H_2S$ release capacity of various liquid samples one to each other (screening method). In that case, no calibration is required. For instance, when a gas chromatography coupled with mass spectrometry is used for the dosing step e), the $H_2S$ release capacity is expressed as a peak-area.

Another object of the present invention is a method for selecting one or more liquid samples among a group of different liquid samples, said method comprising the following steps:
Assessing the $H_2S$ release capacity of each liquid sample according to the method as defined previously;
Selecting one or more liquid samples which have the lowest $H_2S$ release capacity.

This method can be used for instance to identify the liquid sample which has the lowest $H_2S$ release capacity among a group of liquid samples. After assessing the $H_2S$ release capacity of each liquid sample, the samples can be sorted out according to their $H_2S$ release capacity. But this step is not mandatory.

Another object of the present invention is a method for selecting a liquid sample, said method comprising the following steps:
Assessing the $H_2S$ release capacity of each liquid sample according to the method as defined previously;
Comparing the $H_2S$ release capacity with a threshold value.

This method can be used for instance to compare a liquid sample with a reference product or a standard (threshold value).

The methods of the invention can be performed utilizing commercially available devices. Therefore, they are easy to carry out. They can be quantitative or semi-quantitative, and they are fast and effective.

The following examples provide another illustration of the invention but without restraining to the scope of the invention.

EXAMPLES

Example 1

Apparatus and Method

A thermal desorption instrument (TDU, Gerstel) is used with a cooled injection system (CIS-4, Gerstel). The cooled injection system is linked to a gas chromatograph (Agilent, 6890N) coupled to a mass spectrometer (Micro Quattro, Waters). The detection is made in the ionization mode by electronic impact, in mode SIM positif at m/z=34.

As an illustration, a single sulfur containing sample is used as an example to demonstrate the quantitative aspect of the method. The sulfur containing sample tested is thioglycol acid (TGA). Different volumes of TGA are tested (10, 20, 30, 40 and 50 μl) in the thermal desorption instrument 1. Each volume is aged at 50° C., during 5 minutes. A sweeping inert gas (helium, flow rate: 60 mL/min) sweeps the $H_2S$ formed to the cooled injection system 2 wherein $H_2S$ is trapped by cryofocusing, thanks to liquid nitrogen (−100° C.). Once the ageing is finished, the quantity of trapped $H_2S$ is analyzed by the gas chromatograph 3 and the mass spectrometer 4.

Example 2

Results

Figure 2:
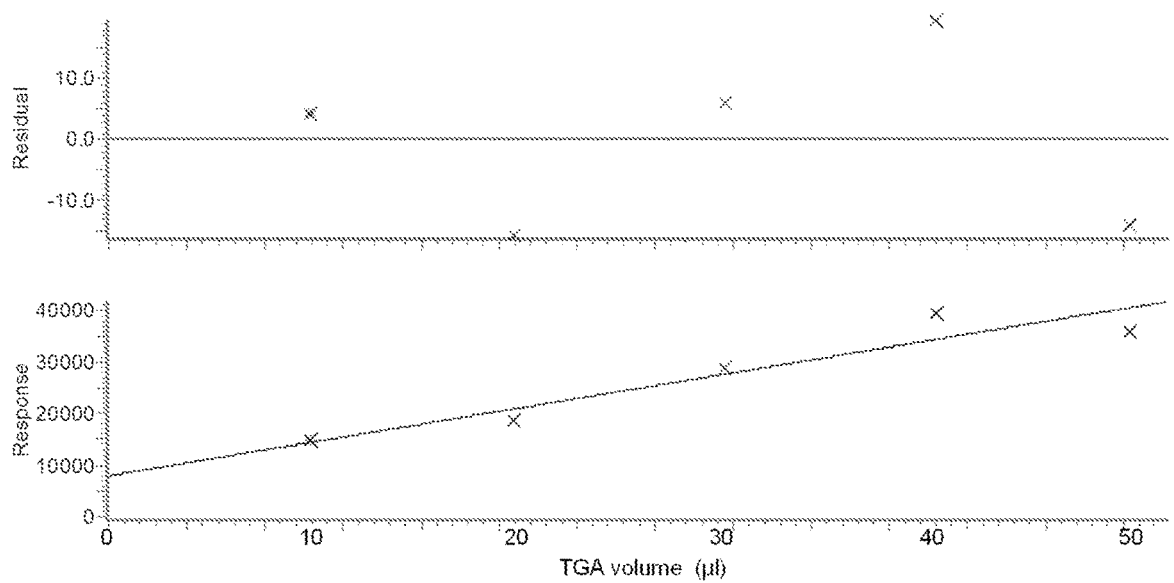
FIG. 2 is a graph illustrating the $H_2S$ release capacity expressed as chromatographic pic area of thioglycol acid as a function of the volume of thioglycol acid, said $H_2S$ release capacity being determined according to the method of the invention.

FIG. 2 shows the area of the peak of $H_2S$ obtained by GC/MS as a function of the volume of sample. The area of the peak of $H_2S$ is proportional to the amount of TGA tested. Other samples may be tested under the same conditions. By comparing the area of the peak of $H_2S$ of each sample, one can easily determine which sample has the lowest $H_2S$ release capacity among the group of samples (screening method).

These results show that the method of the invention enables the rapid and efficient assessment of the $H_2S$ release capacity of liquid sulfur containing samples.

The embodiments above are intended to be illustrative and not limiting. Additional embodiments may be within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

The invention claimed is:

1. A method for measuring the $H_2S$ release capacity of a liquid sample containing one or more sulfur compounds which are able to be degraded into gaseous $H_2S$ with temperature, said method comprising the following steps:
    a) Placing a volume of the liquid sample in a purge vessel so as to obtain a liquid phase and a gaseous phase in a flask;
    b) Purging the gaseous phase with an inert gas stream for a determined period of time;
    c) Passing the purged gaseous phase through a $H_2S$ trap;
    d) Recovering $H_2S$ from the $H_2S$ trap; and
    e) Measuring the recovered $M_2S$,
    wherein the purge vessel is kept at a temperature from 45° C. to 60° C., and
    wherein the liquid sample is a corrosion inhibitor, an oil wetting agent, a solid dispersing agent, a scale inhibitor, an anti-foulant, an oxygen scavenger, a foaming agent, or a mixture thereof.

2. The method according to claim 1, wherein the sulfur compound is a thiol, a thio-ether or a thioacid.

3. The method according to claim 1, wherein the liquid sample has a boiling temperature of at least 80° C.

4. The method according to claim 1, wherein the flow rate of the inert gas stream during steps b) or c) is from 20 mL/min to 90 mL/min.

5. The method according to claim 1, wherein the inert gas is chosen from helium, nitrogen or hydrogen.

6. The method according to claim 1, wherein the period of time of the purging step b) is from 2 min to 12 min.

7. The method according to claim 1, wherein the trapping step c) is performed by cryofocusing, adsorption, absorption, or gas-solid reaction with a captation mass.

8. The method according to claim 1, wherein the measuring step e) is performed by gas chromatography coupled with mass spectrometry, thermogravimetric analysis coupled with mass spectrometry, or elemental analysis for sulfur.

9. A method for selecting a liquid sample among a group of different liquid samples, said method comprising the following steps:
    Measuring the $H_2S$ release capacity of each liquid sample according to the method as defined in claim 1; and
    Selecting the sample which has the lowest $H_2S$ release capacity.

10. A method for selecting a liquid sample, said method comprising the following steps:
    Measuring the $H_2S$ release capacity of each liquid sample according to the method as defined in claim 1; and
    Comparing the $H_2S$ release capacity with a threshold value.

* * * * *

UNITED STATES PATENT AND TRADEMARK OFFICE
CERTIFICATE OF CORRECTION

| | |
|---|---|
| PATENT NO. | : 11,668,692 B2 |
| APPLICATION NO. | : 16/500838 |
| DATED | : June 6, 2023 |
| INVENTOR(S) | : Loriau et al. |

It is certified that error appears in the above-identified patent and that said Letters Patent is hereby corrected as shown below:

On the Title Page

Item (57) In the Abstract, Line 8:
Delete "e)" and insert --c)--.

In the Claims

Column 7, Line 28, Claim 1:
Delete "$M_2S$" and insert --$H_2S$--.

Signed and Sealed this
Thirteenth Day of February, 2024

Katherine Kelly Vidal
*Director of the United States Patent and Trademark Office*